United States Patent [19]

Fischer et al.

[11] Patent Number: 5,008,408
[45] Date of Patent: Apr. 16, 1991

[54] PREPARATION OF 1,4-BUTANEDIOL AND TETRAHYDROFURAN

[75] Inventors: Rolf Fischer, Heidelberg; Juergen Frank, Schwetzingen; Franz Merger, Frankenthal; Hans-Juergen Weyer, Ludwigshafen, all of Fed. Rep. of Germany

[73] Assignee: BASF Aktiengesellschaft, Ludwigshafen, Fed. Rep. of Germany

[21] Appl. No.: 489,709

[22] Filed: Mar. 7, 1990

[30] Foreign Application Priority Data

Mar. 22, 1989 [DE] Fed. Rep. of Germany ....... 3909485

[51] Int. Cl.$^5$ .......................................... C07D 307/08
[52] U.S. Cl. .................... 549/429; 549/472; 549/475; 549/509; 568/861; 568/862
[58] Field of Search ............... 549/472, 475, 509, 429; 568/861, 862

[56] References Cited

U.S. PATENT DOCUMENTS

| | | | |
|---|---|---|---|
| 3,824,219 | 0/1974 | Smith et al. | 260/79.3 R |
| 4,064,145 | 12/1977 | Taylor | 549/509 |
| 4,093,633 | 6/1978 | Tanabe et al. | 549/509 |
| 4,160,771 | 7/1979 | Taylor | 549/509 |

FOREIGN PATENT DOCUMENTS 1595274 5/1970 Fed. Rep. of Germany .
61-197534 9/1986 Japan .

OTHER PUBLICATIONS

Makromolekulare Chemie., Rapid Communications Nr. 7, 5 (1984), 363–371.

Chemiker-Zeitung 101 (1977), pp. 343–350.
C.A. 106, 49.607z (1987).

*Primary Examiner*—Richard L. Raymond
*Attorney, Agent, or Firm*—John H. Shurtleff

[57] ABSTRACT

Mixtures which contain 1,4-butanediol and tetrahydrofuran are prepared by heating 4-hydroxybutyraldehyde of the formula

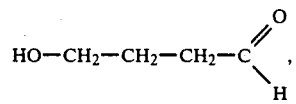

at 20°–300° C. in the presence or absence of 1,4-butanediol and subjecting the resulting acetals of the formulae

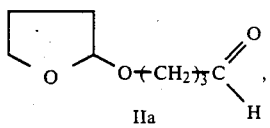

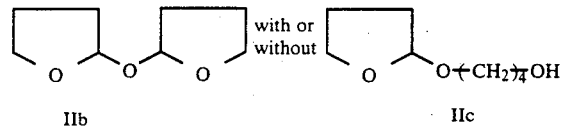

to a catalytic hydrogenation at 50°–300° C. and 1–350 bar.

7 Claims, No Drawings

PREPARATION OF 1,4-BUTANEDIOL AND TETRAHYDROFURAN

The present invention relates to a process for preparing 1,4-butanediol and tetrahydrofuran by converting the 4-hydroxybutyraldehyde into a mixture of the acetals 2-(4-oxobutoxy)tetrahydrofuran and 2,2-oxybistetrahydrofuran, and hydrogenating said mixture to obtain 1,4-butanediol and tetrahydrofuran.

It is known that 4-hydroxybutyraldehyde can be converted by catalytic hydrogenation into 1,4-butanediol which can be cyclized to tetrahydrofuran in the presence of acid catalysts.

We have now found that mixtures of 1,4-butanediol and tetrahydrofuran can be prepared in a particularly advantageous manner by (a) heating 4-hydroxybutyraldehyde of the formula HO—CH$_2$—CH$_2$—CH$_2$—CHO  Ia at 20°–300° C. in the presence or absence of 1,4-butanediol, and (b) subjecting the resulting acetals of the formulae

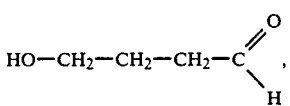
IIa

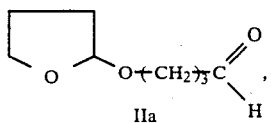
IIb  with or without  IIc to a catalytic hydrogenation at 50°–300° C. and 1–350 bar.

The acetals of the formulae IIa and IIb were known to be formed as byproducts in the reaction of allyl alcohol with carbon monoxide and hydrogen in the presence of phosphine-modified rhodium catalysts. The resulting product mixtures, in addition to the desired 4-hydroxybutyraldehyde, contain 2-methyl-3-hydroxypropionaldehyde, butyrolactone, 2-methyl-3-(tetrahydro-2-furanyloxy)propanol as well as the acetals of the formulae IIa and IIb (see Chem.-Ztg. 101 (1977), 343–50).

As regards the hydrogenation of the acetal of the formula IIa it was known that 97.5% pure 1,4-butanediol containing 0.3% of a mixture of the compound IIa, 1,4-bis(tetrahydro-2-furyloxy)butane and high boilers can be purified at 100° C. by hydrogenation in the presence of a Pd catalyst (JP-A-61/197 534; C.A. 106, 49.607). In the course of said hydrogenation, the level of the mixture of compound IIa, 1,4-bis(tetrahydro-2-furyloxy)butane and high boilers decreases to 0.24%, so that evidently only 0.06% has been converted. It is not stated which compounds are formed in the course of the hydrogenation.

In the novel process of the present invention, 4-hydroxybutyraldehyde, which is in equilibrium with its cyclic hemiacetal of the formula

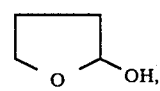
Ib is heated at 20°–300° C., in particular 80°–150° C. The reaction can be carried out batchwise or continuously, under atmospheric, superatmospheric or reduced pressure. To prevent any oxidation of the aldehyde group in the 4-hydroxybutyraldehyde, it can be advantageous to carry out the reaction in the presence of a gas which is inert under the reaction conditions, eg. nitrogen, argon or carbon dioxide. The reaction times for the batchwise reaction range from 0.5 to 6 hours, in particular from 1 to 4 hours.

In a version of the process of the present invention, the 4-hydroxybutyraldehyde is heated in the presence of 1,4-butanediol to form the acetal of the formula IIc which in the course of the hydrogenation according to the present invention is likewise converted into a mixture of tetrahydrofuran and 1,4-butanediol.

The formation of the acetals of the formulae IIa, IIb and IIc can be represented by the following formulae:

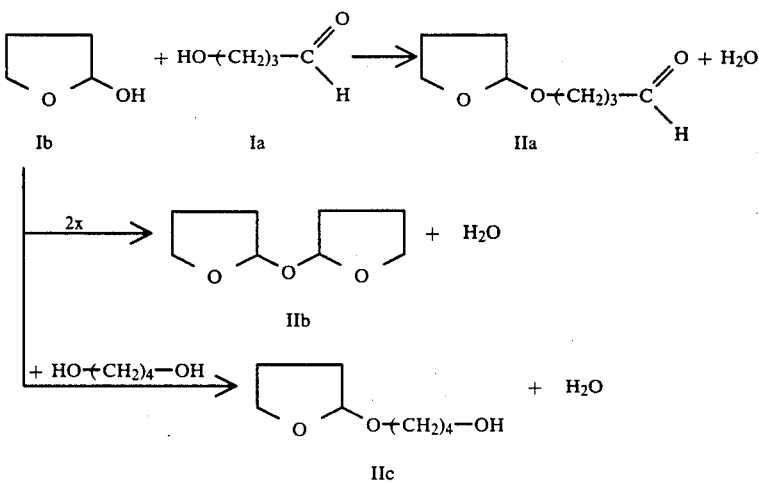

The acetal of the formula IIc is prepared under the same conditions as the acetals IIa and IIb. However, in this version of the process it is advisable to employ an excess of 1,4-butanediol over 4-hydroxybutyraldehyde. For instance, it is advantageous to add from 1 to 5, in particular from 1.5 to 3, moles of 1,4-butanediol to one mole of compounds Ia+Ib.

The reaction of stage (a) can be carried out in the presence of solvents which are inert under the reaction conditions. Possibilities are for example water, aliphatic, cycloaliphatic or aromatic hydrocarbons, such as n-hexane, cyclohexane, methylcyclohexane, benzene or toluene, (hydro)chlorocarbons, such as methylene chloride, chloroform, tetrachloromethane or 1,2-dichloroethane, ethers, such as methyl tert-butyl ether, dioxane or tetrahydrofuran, and mixtures thereof.

If a solvent is used, the starting compound of the formulae Ia/Ib is used as a 1–90% strength by weight solution, in particular as a 5–20% strength by weight solution.

It is a particular advantage of the process according to the present invention that the preparation of the acetals IIa, IIb and IIc does not require the use of a catalyst.

However, to speed up the formation of the acetals IIa and IIb it can be advantageous in some cases to add an acidic agent. Suitable acidic agents are for example sulfonic acids, Lewis acids, non-oxidizing mineral acids, lower fatty acids and acidic cation exchangers. Examples thereof are mineral acids, such as sulphuric acid, hydrochloric acid or hydrobromic acid, sulphonic acids, such as p-toluenesulphonic acid, Lewis acids, such as boron trifluoride or zinc chloride, lower aliphatic carboxylic acids, such as formic acid and acetic acid or propionic acid, zeolites and acidic cation exchangers. Suitable acidic cation exchangers are for example those formed of crosslinked polystyrene having sulfonic acid groups or phenolic resins having sulfonic acid groups.

The acids mentioned are advantageously used in catalytic amounts, for example from 0.001 to 0.25 mole per mole of Ia/Ib. Particular preference is given to strongly acidic cation exchangers.

The reaction mixtures formed in stage (a), which contain the acetals of the formulae IIa and IIb with or without IIc, can be used directly, ie. without prior removal of unconverted 4-hydroxybutyraldehyde, for the subsequent hydrogenation. If the direct option is chosen, it can be advantageous for the hydrogenation, depending on the choice of catalyst, to remove the water of reaction during or after the formation of the acetals IIa and IIb with or without IIc. Since both the acetal IIa and that of the formula IIb are hydrogenable to tetrahydrofuran and 1,4-butanediol, there is no need to separate these compounds before the hydrogenation.

However, the acetals of the formulae IIa, IIb and IIc can also be isolated from the reaction mixtures of stage (a) before the hydrogenation. For instance, the acetals formed can be separated from the unconverted starting compound (Ia/Ib) and the water of reaction by distillation, with or without removal of the acidic agents mentioned, which may be removed in a conventional manner, for example by neutralization, distillation or filtration. To work up the acetal of the formula IIc, all or some of the 1,4-butanediol present in the reaction mixture can be separated off and disposed of or recycled into the synthesis.

To maximize the conversion of the starting material Ia/Ib, it can be advantageous to remove the water of reaction from the reaction mixture continuously by distillation. If a solvent which forms an azeotrope with water has been used, it can be distilled out of the reaction mixture together with the water.

The hydrogenation of the acetals of the formulae IIa, IIb and IIc according to the present invention may be represented by the following scheme:

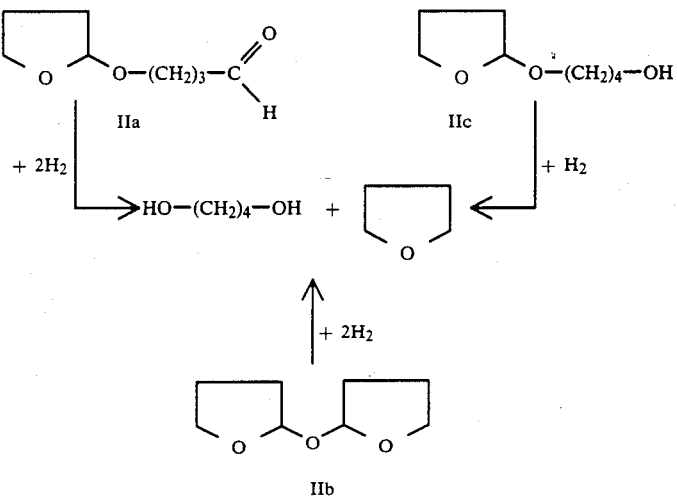

Besides 1,4-butanediol and tetrahydrofuran a minor amount of 4,4'-dihydroxydibutyl ether, HO—(CH$_2$)$_4$—O—(CH$_2$)$_4$—OH, is formed. This etherdiol is suitable for preparing polyesters and, owing to the preferential formation of tetrahydrofuran, cannot be prepared by condensing two molecules of 1,4-butanediol.

The hydrogenation is carried out at 50°–300° C., in particular 100°–260° C., and at 1–350 bar, in particular 100–300 bar. It is carried out in the gas or liquid phase. The hydrogenation is carried out batchwise or preferably continuously as a liquid phase or trickle bed procedure over a fixed bed or suspended catalyst. Suitable weight hourly space velocities over the catalyst range from 0.05 to 1, in particular from 0.1 to 0.5, kg of IIa+IIb per liter of catalyst per hour. The reactors used can be for example tubular reactors or tube bundle reactors. The catalysts used can be conventional hydrogenation catalysts.

Preferred hydrogenation catalysts are those which contain copper and/or elements of subgroup VIII of the periodic table of the elements, in particular nickel, cobalt, palladium, platinum, rhodium and/or ruthenium.

The catalysts are used in the form of supported or solid catalysts. Supported catalysts are prepared in a conventional manner, advantageously by impregnating the carrier material one or more times with an aqueous solution of the metal salts, drying and heating the catalytic material to convert the metal salts into the oxides. Before use the catalysts are treated with hydrogen to reduce the bulk of the oxides to the metals. Suitable catalyst carriers are for example silicon dioxide, aluminum oxide, titanium dioxide, activated carbon, silicates and zeolites. If necessary, the catalysts can be prepared using binders, for example graphite.

4-Hydroxybutyraldehyde is obtainable for example by hydroformylation of allyl alcohol in the presence of rhodium complexes, by anodic oxidation of tetrahydrofuran (DE-A-3 615 472) or by isomerization of 2-butene-1,4-diol using rhodium compounds (DE-A-3 718 897).

EXAMPLES

Example 1

(a) Preparation of the Acetals of the Formulae IIa and IIb 40 g of a 4-hydroxybutyraldehyde prepared as described in DE-A-3 718 897 were heated at the boil (124° C.) under nitrogen for three hours. The reaction mixture was then cooled down and analyzed by GC. Its composition was found to be 24% unconverted 4-hydroxybutyraldehyde, 11% acetal of the formula IIb and 64% acetal of the formula IIa (each percent symbol denoting mol %, based on starting 4-hydroxybutyraldehyde). Fractional distillation gave 8.3 g of 4-hydroxybutyraldehyde (21%) of boiling point 77° C./33 mbar and 25.3 g of a mixture of the acetals of the formulae IIa and IIb (71%) of boiling point 98°-118° C./27-33 mbar.

This reaction was carried out at various temperatures. The reaction conditions and results are summarized in the following table:

| Reaction temp. (°C.) | Reaction time (h) | Mol % (2) HBA (1) | II a | II b | Selectivity (%) |
|---|---|---|---|---|---|
| 80 | 6 | 59 | 21 | 17 | 93 |
| 100 | 6 | 36 | 42 | 21 | 98 |
| 120 | 6 | 26 | 52 | 21 | 99 |

(1) HBA = 4-hydroxybutyraldehyde
(2) quantitative GC analysis (b) Preparation of the Acetal of the Formula IIc 20 g of a 4-hydroxybutyraldehyde prepared as described in DE-A-3 718 897 were heated under nitrogen at 120° C. together with 41.4 g of 1,4-butanediol for three hours. Analysis by gas chromatography revealed that the reaction mixture contained 44% of the acetal of the formula IIc, 41% of 1,4-butanediol and 2% of unconverted 4-hydroxybutyraldehyde.

(c) Hydrogenation 120 g of a mixture of the acetals of the formulae IIa (85%) and IIb (15%) obtained as per section (a) were hydrogenated at 175° C. and 200 bar in the presence of 14 g of a hydrogen-activated copper catalyst (55.6% of CuO, 43.6% of Al$_2$O$_3$) for 10 hours. The reacted mixture was distilled to yield 66.5 g of tetrahydrofuran, 46.5 g of 1,4-butanediol and 2.5 g of 4,4'-dihydroxybutyl ether.

Example 2 (Comparison)

The hydrogenation of section (c) of Example 1 was repeated, except that the starting mixture was replaced by 120 g of freshly distilled 4-hydroxybutyraldehyde. Analysis of the reacted mixture by gas chromatography found 51.7 g of 1,4-butanediol and only 1.3 g of tetrahydrofuran.

Example 3

120 g of the acetal mixture used in section (c) of Example 1 were hydrogenated at 190° C. and 200 bar in the presence of 11 g of a hydrogen-activated cobalt catalyst (63.4% of CoO, 18.1% of CuO, 6.8% of Mn$_3$O$_4$, 3.1% of MoO$_3$, 3.3% of P$_2$O$_5$, 0.2% of Na$_2$O) for 15 hours. Analysis by gas chromatography revealed that complete conversion produced 53.9 g of tetrahydrofuran, 62.3 g of 1,4-butanediol and 1.8 g of 4,4'-dihydroxydibutyl ether.

Example 4 (Comparison)

The hydrogenation of Example 3 was repeated, except that the acetal mixture was replaced by 120 g of freshly distilled 4-hydroxybutyraldehyde. Analysis of the reacted mixture by gas chromatography found only 15 g of 1,4-butanediol and 0.6 g of tetrahydrofuran.

Example 5

10 g of a mixture of 2-(4-hydroxybutoxy)tetrahydrofuran of the formula IIc (83%) and 1,4-bis(2-tetrahydrofuranyloxy)butane (17%) obtained as described in section (b) of Example 1 were hydrogenated at 100° C. and 150 bar in the presence of 1 g of a palladium catalyst (10% of Pd on activated carbon) for 10 hours. Discharged from the autoclave, the reacted mixture was analyzed by gas chromatography and found to contain 20.7% of tetrahydrofuran, 38.4% of 1,4-butanediol, 29.6% of 4,4'-dihydroxy-dibutyl ether and 7.4% of 5,10-dioxatetradecane-1,14-diol.

We claim:

1. A two-stage process for preparing a mixture which contains 1,4-butanediol and tetrahydrofuran, which comprises:

(a) heating 4-hydroxybutyraldehyde of the formula $$HO-CH_2-CH_2-CH_2-C\overset{\displaystyle O}{\underset{\displaystyle H}{\diagdown}} \quad \text{Ia}$$

at 20°-300° C. in the presence or absence of 1,4-butanediol, and in the presence or absence of an acidic agent; and (b) after removing the water of reaction and any acidic agent, subjecting the resulting acetals of the formulae IIa -continued

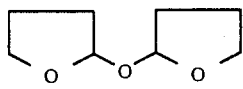 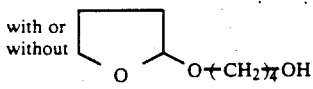

IIb                    IIc to a catalytic hydrogenation at 50°–300° C. and 1–350 bar.

2. A process as claimed in claim 1, wherein the reaction of stage (a) is carried out in the presence of a solvent which is inert under the reaction conditions.

3. A process as claimed in claim 1, wherein the reaction of stage (a) is carried out with continuous removal of the water of reaction.

4. A process as claimed in claim 1, wherein the reaction of stage (a) is carried out in the presence of an acidic catalyst.

5. A process as claimed in claim 1, wherein the hydrogenation of stage (b) is carried out in the presence of a catalyst which contains copper and/or an element of subgroup VIII of the periodic table of the elements.

6. A process as claimed in claim 1, wherein the hydrogenation of stage (b) is carried out without the prior removal of unconverted 4-hydroxybutyraldehyde.

7. A process as claimed in claim 1, wherein the reaction stage (a) is carried out in the absence of any acidic agent.

* * * * *